(12) United States Patent
Yao et al.

(10) Patent No.: US 7,931,638 B2
(45) Date of Patent: Apr. 26, 2011

(54) DIAPERS HAVING A ZONED NON-ATTACHABLE BACK SHEET AND METHODS OF MANUFACTURING SAME

(75) Inventors: Min Yao, Vernon Hills, IL (US); Daniel B. Love, Libertyville, IL (US)

(73) Assignee: Medline Industries, Inc., Mundelein, IL (US)

(*) Notice: Subject to any disclaimer, the term of this patent is extended or adjusted under 35 U.S.C. 154(b) by 321 days.

(21) Appl. No.: 12/233,249

(22) Filed: Sep. 18, 2008

(65) Prior Publication Data
US 2010/0069875 A1 Mar. 18, 2010

(51) Int. Cl.
*A61F 13/15* (2006.01)
(52) U.S. Cl. ........ 604/389; 604/391; 604/378; 604/387; 604/367
(58) Field of Classification Search .............. 604/389, 604/391, 378, 387, 367
See application file for complete search history.

(56) References Cited

U.S. PATENT DOCUMENTS

| | | | |
|---|---|---|---|
| 4,662,875 A | 5/1987 | Hirotsu et al. | |
| 4,704,114 A | 11/1987 | Wilson et al. | |
| 4,847,134 A | 7/1989 | Fahrenkrug et al. | |
| 4,894,060 A * | 1/1990 | Nestegard | 604/391 |
| 5,133,707 A * | 7/1992 | Rogers et al. | 604/389 |
| 5,304,162 A | 4/1994 | Kuen | |
| 5,411,498 A | 5/1995 | Fahrenkrug et al. | |
| 5,496,298 A | 3/1996 | Kuepper et al. | |
| 5,527,302 A | 6/1996 | Endres et al. | |
| 5,706,524 A | 1/1998 | Herrin et al. | |
| 5,873,870 A | 2/1999 | Seitz et al. | |
| 5,873,871 A * | 2/1999 | Lavash et al. | 604/386 |
| 5,885,656 A | 3/1999 | Goldwasser | |
| 5,926,926 A | 7/1999 | Kato | |
| 5,957,908 A | 9/1999 | Kline et al. | |
| 6,086,571 A | 7/2000 | Guevara et al. | |
| 6,352,528 B1 | 3/2002 | Weber et al. | |
| 6,544,244 B1 | 4/2003 | Glaug et al. | |
| 6,589,638 B1 | 7/2003 | McCormack et al. | |
| 6,675,702 B1 | 1/2004 | Maksimow | |
| 6,905,488 B2 | 6/2005 | Olson | |

(Continued)

OTHER PUBLICATIONS

Written Opinion corresponding to co-pending International Patent Application Serial No. PCT/US2009/057502, International Searching Authority; dated Nov. 6, 2009; 5 pages.

(Continued)

*Primary Examiner* — Jacqueline F Stephens
(74) *Attorney, Agent, or Firm* — Nixon Peabody LLP

(57) ABSTRACT

According to one embodiment, an absorbent article to be worn about a wearer has a front portion and a back portion. The absorbent article includes an outer layer, an inner layer that is substantially co-extensive with the outer layer, an absorbent layer and one or more fasteners, which are located on the back portion of the absorbent article. The absorbent layer is interposed between the outer layer and the inner layer to form the absorbent article. The outer layer has a central portion between two side portions. The central portion of the outer layer is treated with a chemical to substantially inhibit attachment of the one or more fasteners to the central portion of the outer layer. The one or more fasteners secure the back portion to the outer layer of the front portion. Specifically, the one or more fasteners are configured to secure the back portion to a region of the outer layer which is not treated with the chemical.

8 Claims, 5 Drawing Sheets

U.S. PATENT DOCUMENTS

| | | |
|---|---|---|
| 6,969,377 B2 | 11/2005 | Koele et al. |
| 6,989,339 B2 | 1/2006 | Eden et al. |
| 7,198,621 B2 | 4/2007 | Moser et al. |
| 7,237,370 B1 | 7/2007 | Garone et al. |
| 2001/0041879 A1 | 11/2001 | Karami et al. |
| 2003/0100879 A1 | 5/2003 | Kline et al. |
| 2005/0154366 A1 | 7/2005 | Karami et al. |
| 2006/0189956 A1 | 8/2006 | Catalan |
| 2007/0142798 A1 | 6/2007 | Goodlander et al. |
| 2007/0142806 A1 | 6/2007 | Roe et al. |

OTHER PUBLICATIONS

International Search Report corresponding to co-pending International Patent Application Serial No. PCT/US2009/057502, International Searching Authority; dated Nov. 6, 2009; 2 pages.

* cited by examiner

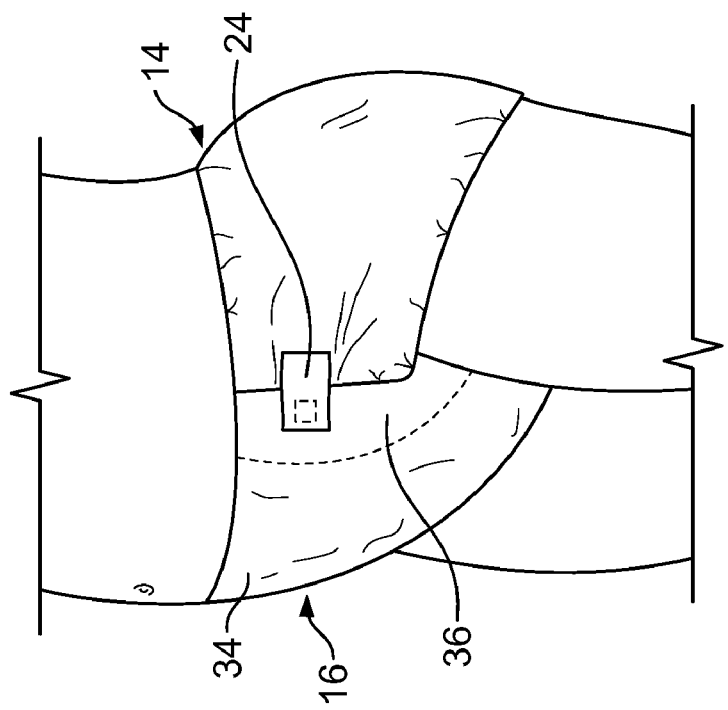
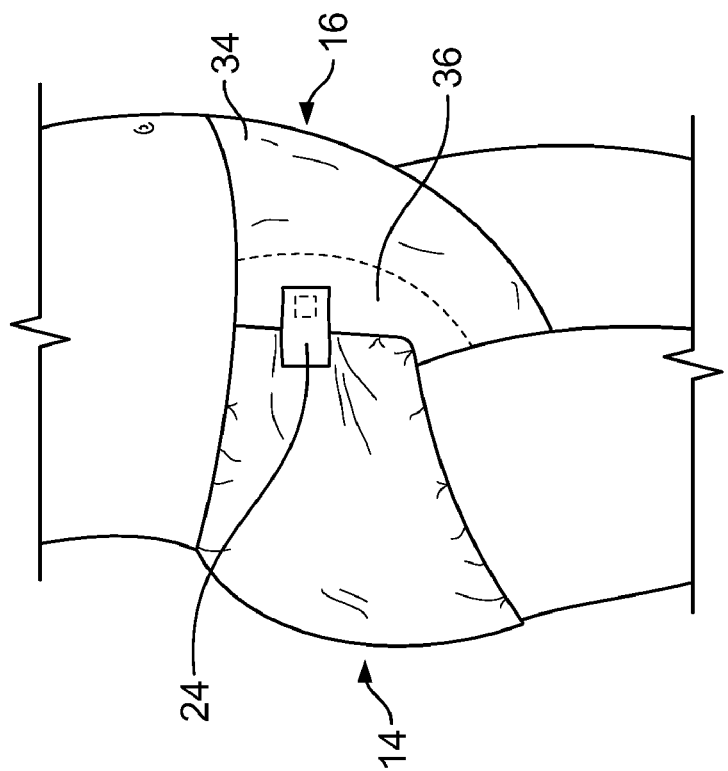

DIAPERS HAVING A ZONED NON-ATTACHABLE BACK SHEET AND METHODS OF MANUFACTURING SAME

FIELD OF THE INVENTION

The present invention relates generally to an absorbent article and, in particular, a disposable diaper or incontinence brief that requires a wearer or caregiver to select an appropriately-sized disposable diaper or incontinence brief for the wearer.

BACKGROUND

Adult incontinence briefs, disposable diapers, and other absorbent articles are designed to absorb and contain liquid and other discharges from the human body to prevent body and clothing soiling. Often, an ill-fitting absorbent article is chosen for a wearer. One reason for the ill-fit is due to the fact that the size determination of absorbent articles is often based on a single criteria such as a wearer's weight, hip circumference, or waist circumference. Thus, other relevant factors such as age, height, thigh circumference, and rise are not taken into account. Alternatively, a wearer or caregiver may purposely choose a larger-sized absorbent article under the mistaken belief that it will have a greater absorbency and, hence, be more beneficial. In reality, however, an oversized absorbent article may slip, slide, sag, or droop, any of which may cause discomfort and/or leakage.

Unlike determining that an absorbent article is too small for a wearer, determining that an absorbent article is too large for a wearer can be difficult and problematic. It is evident when an absorbent article is too small for a wearer because the fastening components, typically located on a back portion of the absorbent article, will not sufficiently reach the front portion of the absorbent article, thus making it impossible to secure the absorbent article to the wearer. In contrast, when an absorbent article is too large for a wearer, the back portion may be wrapped around the wearer's waist such that the fastening components may be attached anywhere on the back sheet (i.e., the exterior of the absorbent article) of the absorbent article. Because wearers of absorbent articles are often very young children or elderly persons, the wearers may be unable to walk or move freely and therefore may be unlikely to notice the absorbent article sagging or drooping. Moreover, the wearer may not be able to effectively communicate to his or her caregiver that the absorbent article is too large. In other cases, the ill-fit may be relatively subtle, leading the wearer to mistakenly believe that a proper fitting absorbent article was chosen.

Downsizing an absorbent article has several benefits to the wearer. First, downsizing to an absorbent article that provides a better fit is likely to reduce leakage as the smaller absorbent article will be less likely to slip, slide, sag, or droop. Moreover, downsizing an absorbent article may be more cost effective. Larger-sized absorbent articles are typically more expensive than smaller-sized absorbent articles of comparable absorbency. This is due to the fact that larger absorbent articles require the use of more absorbent materials and are, thus, more costly to manufacture. Often, a case of larger-sized absorbent articles will cost the same as smaller-sized absorbent articles but will contain considerably fewer absorbent articles.

Therefore, there exists a need for an absorbent article that requires or forces a wearer or caregiver to select a properly-fitting absorbent article.

BRIEF DESCRIPTION OF THE DRAWINGS

The foregoing and other advantages of the invention will become apparent upon reading the following detailed description and upon reference to the drawings.

FIGS. 3A and 3B illustrate a right and a left side view, respectively, of the diaper of FIG. 1.

Figure 1:
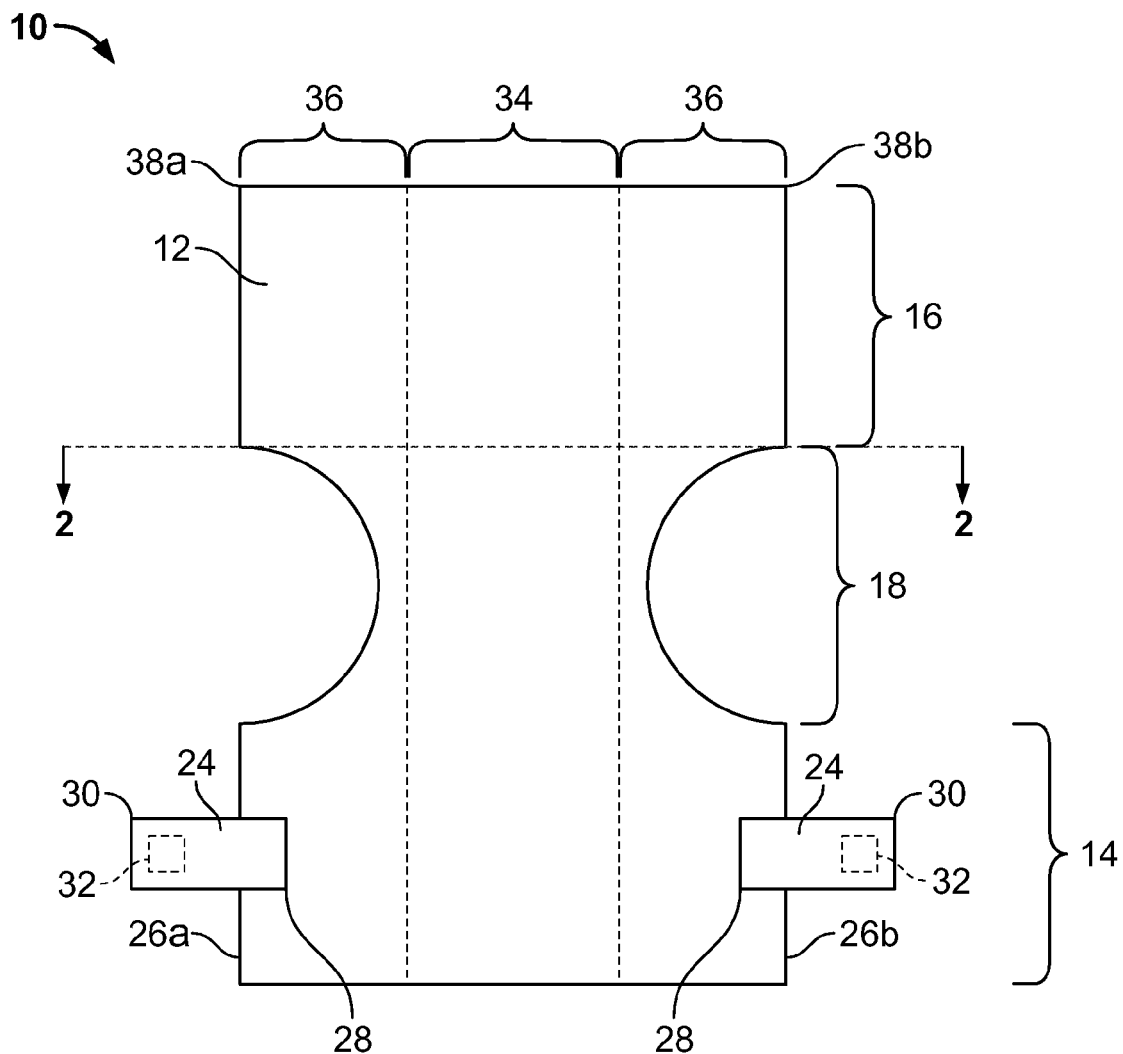
FIG. 1 illustrates a top view of an outer layer of a disposable diaper according to one embodiment.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention.

DESCRIPTION OF ILLUSTRATIVE EMBODIMENTS

Absorbent articles described herein generally include an outer layer that is zone-treated with a chemical to require a wearer or caregiver to select a properly-fitting absorbent article for the wearer. Although the remainder of the description of the illustrative embodiments will be specifically directed toward a disposable diaper, it is to be understood that the embodiments may also be implemented for other absorbent articles such as, for example, adult incontinence briefs and that the properties and uses described below apply to these other absorbent articles as well.

Referring to FIG. 1, a top view of a disposable diaper 10 according to one embodiment is illustrated. The diaper 10 is of a substantially rectangular configuration to fit comfortably around a wearer; however, it is contemplated that any other suitable configuration can be employed. The diaper includes a middle portion 18 located between a back portion 14 and a front portion 16. The middle portion 18 is contoured in an "hourglass" configuration to fit comfortably around a wearer's thighs when the diaper 10 is secured to the wearer.

Figure 2:
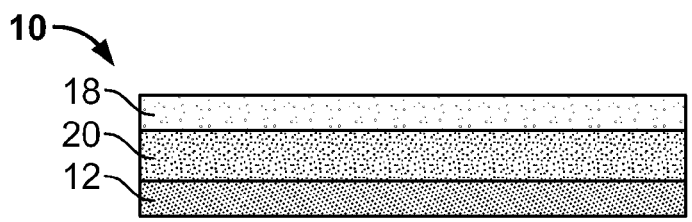
FIG. 2 illustrates a cross-section view generally taken through section line 2-2 of the diaper of FIG. 1.

The diaper 10 generally consists of several layers, as shown in FIG. 2. FIG. 2 is a cross-sectional view of the diaper 10 generally along section line 2-2 shown in FIG. 1. The diaper 10 includes an inner layer 20, which faces a wearer when the diaper 10 is secured to the wearer. The inner layer 20 can be a non-woven, permeable fabric made from any suitable material such as, for example, polypropylene, polyethylene, polyester, materials having hydrophobic properties, combinations thereof and/or the like. Additionally, the inner layer 20 can be treated with a hydrophilic finish to improve pass through of liquids to diaper layers beneath the inner layer 20. Non-limiting examples of suitable hydrophilic finishes include anonic surfactants, catonic surfactants, nonionic surfactants, wetting agents (e.g., silicon based surfactants, glycol based surfactants), combinations thereof and/or the like. As will be discussed in greater detail below, the inner layer 20 is typically formed from a plastic resin of any of the above-referenced materials.

The diaper 10 also includes a non-woven, liquid-impervious outer layer 12, which faces away from the wearer when the diaper 10 is secured to the wearer. The outer layer 12 may be made of any material suitable to minimize or prevent fluids and other discharge from escaping the diaper. Non-limiting examples of suitable materials for the outer layer 12 include polyethylene and/or breathable poly. According to some embodiments, the outer layer 12 can be a thin film such as, for example, polyethylene film. As will be discussed in greater detail below, the outer layer 12 is formed by any process that is suitable to form a non-woven fabric of fibrous loops. This outer layer 12 is substantially co-extensive with the inner layer 20.

An absorbent layer 22 is positioned between the inner layer 20 and the outer layer 12. The absorbent layer 14 may be composed of any materials suitable for absorbing bodily fluids and discharge including, but not limited to, a fibrous material (e.g., fluffed wood pulp), a super absorbent polymer (SAP), or the combination of SAP and a fibrous material. The SAP can be natural or synthetic and may be biodegradable. Non-limiting examples of SAP include polymers based on acrylate(s) such as sodium acrylate, potassium acrylate, and/or an alkyl acrylate(s) (e.g., methyl acrylate, ethyl acrylate, propyl acrylate, butyl acrylate, and hexyl acrylate). The absorbency of the diaper 10 may vary depending upon whether it is intended for use by infants, children and/or adults.

Referring back to FIG. 1, a top view of the outer layer 12 of the diaper 10 is shown. The diaper 10 includes features designed for securing the diaper 10 to a wearer. For example, the diaper 10 has fastening components 24 positioned on opposite sides 26a, 26b of the diaper 10. Each of the fastening components 24 has a fixed end 28 and a free end 30. The fixed end 28 can be secured to the inner layer 20, the outer layer 12, or both. The free end 30 extends outwards beyond the fixed end 28 in a transverse direction. The free end 30 includes a fastener member 32 comprising a plurality of hooks that are suitable to engage and attach to the fibrous loops inherent in the outer layer 12. The plurality of hooks are configured to provide adequate strength of attachment such that the fastener member(s) 32 remains attached to the outer layer 12 under ordinary conditions of diaper use. The fastener member(s) 32 can be made from suitable materials such as, for example, nylon, polyester, polyamide, combinations thereof, and/or the like. In the embodiment shown in FIG. 1, the fixed ends 28 are secured to the back portion 14, thus allowing the free ends 30 to contact and attach to the outer layer 12 of the front portion 16 when the diaper is folded and positioned on a wearer, as shown in FIGS. 3A and 3B.

It is contemplated that in alternative embodiments the fastening components 24 may have a fixed end 28 secured to the front portion 16 and a free end 30 for attachment to the back portion 14; however, it may be more convenient to fix the fastening components 24 to the back portion 14 as described above with respect to FIGS. 1, 3A and 3B. It is further contemplated that according to some embodiments, the fastening components 24 may be integrally formed with the inner layer 20, the outer layer 12, or both. According to other embodiments, the fastening components 24 may not include a fixed end 28. Rather, the fastening components 24 may have two free ends 30, each free end 30 including a fastener member 32, with one free end 30 attached to the front portion 16 and the other free end 30 attached to the back portion 14. While the embodiment described with respect to FIG. 1 includes two fastening components, it is contemplated that any number of fastener components can be provided.

Referring again to FIG. 1, the outer layer 12 has a central portion 34 located between two side portions 36. The central portion 34 of the outer layer 12 is treated with a chemical coating. The chemical coating generally alters some of the functional properties of the fibers in the central portion 34. In particular, the chemical coating substantially inhibits or prevents the hooks of the fastener members 32 from attaching to the fibrous loops of the central portion 34. Non-limiting examples of suitable chemical coatings include urethanes, acrylic, vinyls, epoxies, silicone binders, fluorocarbon polymers (e.g., polytetrafluoroethylene (PTFE)), combinations thereof and/or the like.

The chemically-treated central portion 34 forces a wearer or a caregiver securing the diaper 10 to the wearer to downsize the diaper 10 when the diaper 10 is too large for the wearer. In order to secure the diaper 10 to the wearer, the side edges 26a, 26b of the back portion 14 are grasped and pulled in opposite directions, laterally and outwardly, stretching the back portion 14 so that it lies flat and snug against the wearer. As used herein, the word "snug" refers to a fitting of the diaper that is comfortable for the wearer, yet tight enough to hold the diaper secured to the wearer under ordinary diaper use conditions. Each of the sides 26a, 26b should be pulled with generally the same amount of force so that the diaper 10 remains positioned generally evenly and symmetrically on the wearer. The side edges of the front portion 38a, 38b are also pulled so that the front portion 16 lies flat and snug against the wearer's abdomen. The free ends 30 of the fastening components 24 are pressed to a section of the front portion 16 of the diaper 10 located as far around the wearer's waist as the free ends 30 will comfortably reach so that the side edges 26a, 26b of the back portion 14 overlap the side edges 38a, 38b of the front portion 16.

If, after the free ends 30 are pressed to the outer layer 12 of the front portion 16, the fastener members 32 remain attached to the outer layer 12, the correct size diaper 10 has been chosen. FIGS. 3A and 3B show the diaper 10 of FIG. 1 being properly fit to the wearer. On the other hand, if the fastener members 32 do not attach to the outer layer 12, the diaper 10 is too large for the wearer. Because the hooks of the fastener members 32 cannot attach to the loops of the chemically-treated central portion 34 of the outer layer 12, the wearer or caregiver is forced to downsize to a properly-fitting diaper.

In one embodiment, a diaper 10 designed to fit a waist size of about 59 inches (about 150 cm) to about 66 inches (about 168 cm) includes a central portion 34 having a width (i.e., parallel to the wearer's waist) of about 7 inches (about 18 cm) and a length (i.e., perpendicular to the wearer's waist) of about 37 inches (about 94 cm). In another embodiment, a diaper 10 designed to fit a waist size of about 32 inches (about 81 cm) to about 42 inches (about 107 cm) includes a central portion 34 having a width of about 7 inches (about 18 cm) and a length of about 31 inches (about 79 cm). These dimensions are intended as non-limiting examples and it is contemplated that any other suitably-sized central portion 34 may be utilized.

It is contemplated that according to alternative embodiments, the chemical coating can also include a colorant. As a result, the chemically-treated central portion 34 would also provide a visual indicator of whether the diaper is properly-sized in addition to physically preventing a wearer or a caregiver from choosing an ill-fitting diaper.

It is also contemplated that the central portion 34 of the outer layer 12 can be shaped and sized according to configurations that are different than that illustrated in FIG. 1. For example, the central portion 34 may be applied only to the front portion 16 of the outer layer 12. As another example, the central portion 34 may comprise two chemically-treated portions with an untreated portion therebetween.

Figure 4:
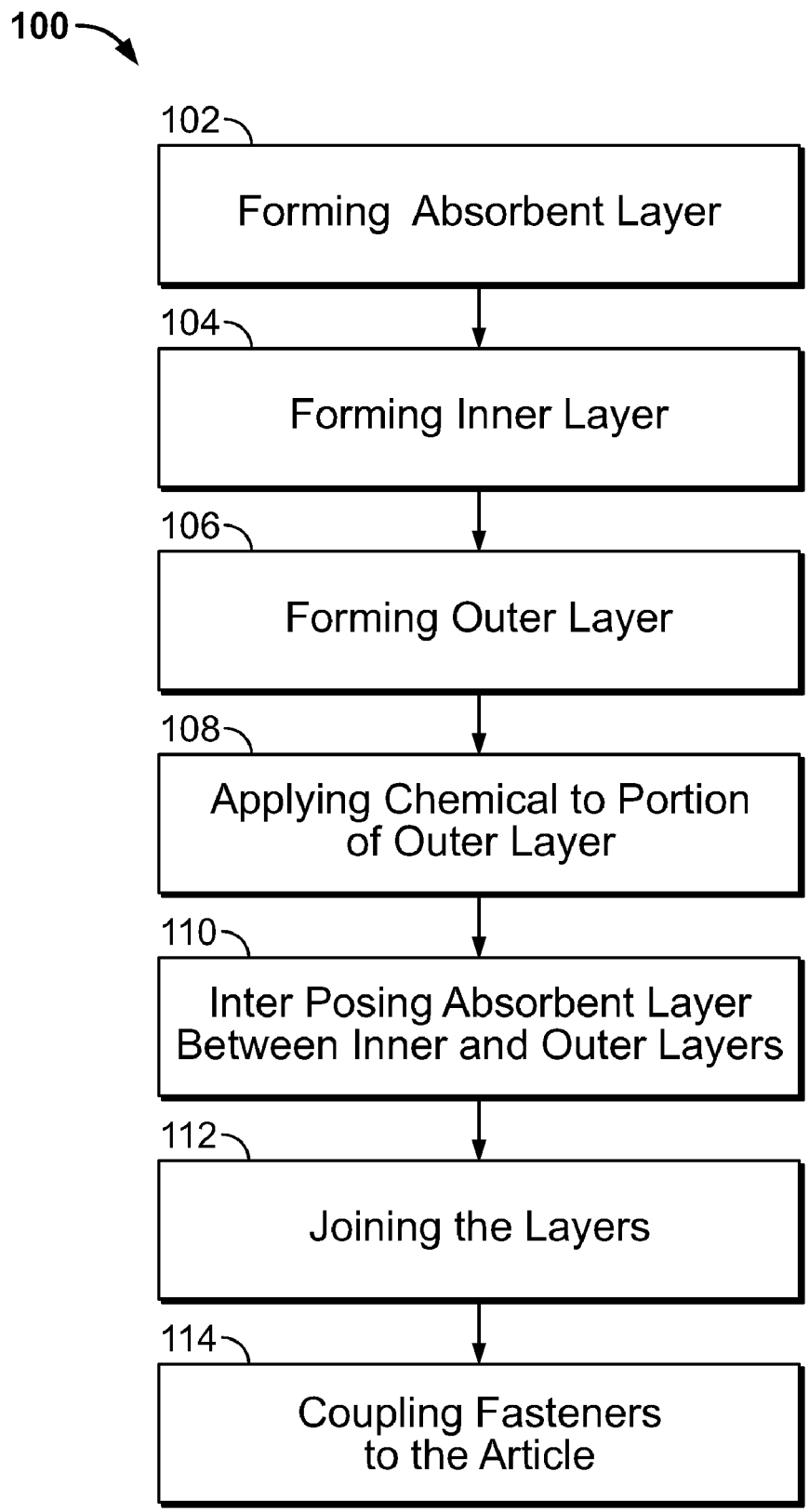
FIG. 4 illustrates an operational flow diagram for manufacturing a disposable diaper according to one embodiment.

Referring to FIG. 4, a diagram illustrates the operational flow for manufacturing an absorbent article such as a disposable diaper according to some embodiments. In its most basic form, the method of manufacturing a diaper 100 includes forming an absorbent layer 22 (block 102), forming an inner layer 20 (block 104), forming an outer layer 12 (block 106), treating a central portion 34 of the outer layer 12 with a chemical coating (block 108), interposing the absorbent layer 22 between the outer layer 12 and the inner layer 20 (block 110), joining the inner layer 20, absorbent layer 22 and outer layers 12 (block 112), and coupling fastening components 24a, 24b to the diaper 10 (block 114). Each of these steps will now be described in more detail.

At block 102, the absorbent layer 22 can be formed from the super absorbent polymers and fibrous material(s) by any suitable process. For example, the absorbent layer 14 can be formed on a conveyor belt passing under a series of pressurized nozzles. Depending upon the desired densities and distributions of SAP and fibrous material within the absorbent layer 14, a particular pressurized nozzle in the series of pressurized nozzles may spray SAP particles, fibrous material, or a mixture of SAP and fibrous material onto the conveyor surface. The bottom of the conveyor belt surface is perforated and a vacuum is applied from below so that the fibers are pulled down to form a long flat absorbent pad as the materials are sprayed onto the conveyor belt. An absorbent pad of uniform thickness can be achieved by a leveling roller used to remove a portion of the SAP and/or fibrous material(s). The result of this process is a long uniform pad of absorbent material ("an absorbent pad") that is subsequently cut to form the absorbent layer 22.

At blocks 104 and 106, the inner layer 20 and the outer layer 12 are formed by any dry laid or wet laid process. For example, the inner layer 20 and the outer layer 12 may be formed by a melt blown process, spunbond process, spunlace process, spunlaid process or the like. According to a melt blown process, a plastic resin (e.g., polypropylene, polyester, polylactic acid resin, or polyethylene) is melted and extruded though small holes by air pressure. The fibers condense onto a sheet as the air-blown stream of fibers cools. Heated rollers are then used to flatten the fibers and bond them together. The result is a "web" of nonwoven fabric, which can be rolled to form a bolt of fabric. Thus, an inner web is the web of fabric comprising the inner layer 20 of a diaper 10 and the outer web is the web of fabric comprising the outer layer 12 of the diaper 10.

Figure 5A:
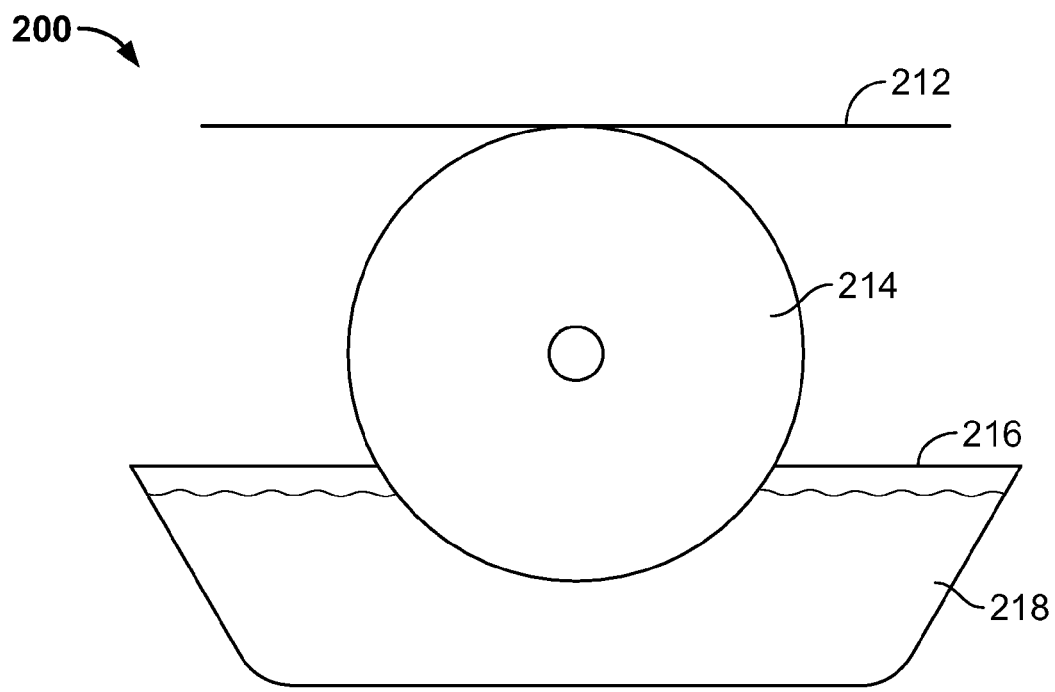
FIG. 5A illustrates a side view of a kiss roll process according to one embodiment.
Figure 5B:
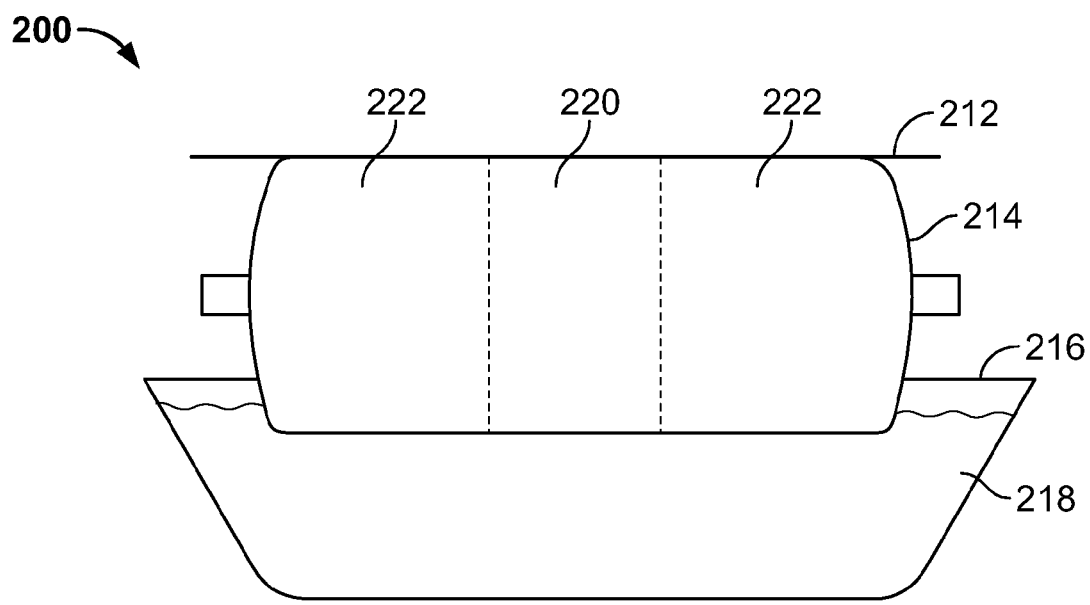
FIG. 5B illustrates a front view of a kiss roll process according to one embodiment.

At block 108, the web of fabric comprising the outer layer 12 of a diaper ("the outer web") is treated with a chemical coating by any suitable process such as, for example, a kiss roll coating process, a slot die coating process, or a spraying process. A kiss roll process 200 is illustrated in FIGS. 5A and 5B. A coating roll 214 is disposed below the outer web 212. A trough 216 containing the chemical coating 218 is disposed beneath the coating roll 214 such that a lower portion of the coating roll 214 is immersed in the chemical coating 218. As the outer web 212 is transported past the coating roll 214, the coating roll 214 rotates to carry a metered film of chemical coating 218 into contact with the outer web 212.

The outer web 212 will eventually be cut into smaller pieces to produce an outer layer 12 for a plurality of diapers. To ensure that only the central portion 34 of an outer layer 12 produced from the outer web 212 is treated with the chemical coating 218, the coating roll 214 is partitioned into one or more coating portions 220 and non-coating portions 222. Accordingly, the coating portions 220 are disposed beneath portions of the outer web 212 to which the chemical coating 218 is applied and non-coating portions 222 are disposed beneath portions of the outer web 212 to which the chemical coating is not applied.

As shown in FIG. 5B, the coating roll 214 includes a coating portion 220 located between two non-coating portions 222. The coating portion 220 of the coating roll 214 has a width corresponding to the width of a central portion 34 of an outer layer 12 that will be produced from the outer web 212. The non-coating portions 222 are designed to prevent or minimize the amount of chemical coating 218 applied to the outer web 212. For example, the non-coating portions 222 can be wrapped with a fabric that either has inherent hydrophobic properties or is treated with a hydrophobic chemical. Non-limiting examples of hydrophobic fabrics include polypropylene fabric, polyethylene fabric and polyester fabric. The hydrophobic fabric may be a non-woven fabric. Non-limiting examples of hydrophobic chemicals for use with the fabric on the non-coating portions 222 include stearic acid, melamine based chemicals, fluorocarbon chemicals, and silicon based chemicals. When wrapped with a hydrophobic fabric, a minimal amount of chemical coating 218 is picked up by the non-coating portions 222. Much of the chemical coating 218 that is picked up quickly beads off of the non-coating portions 222. As a result, only a negligible amount, if any, of the chemical coating 218 is brought into contact with the outer web 212 by the coating roll 214.

It is contemplated that two or more coating rolls can be positioned side by side across the width of the outer web. Additionally, a coating roll may have one or more coating portions, any number of non-coating portions, or no non-coating portions at all. These variations may be advantageous when multiple outer layers are to be produced across the width of the outer web. It is further contemplated that multiple coating rolls may be employed at intervals along the transport path of the outer web to apply multiple coatings of the chemical coating to the outer web.

Figure 6:
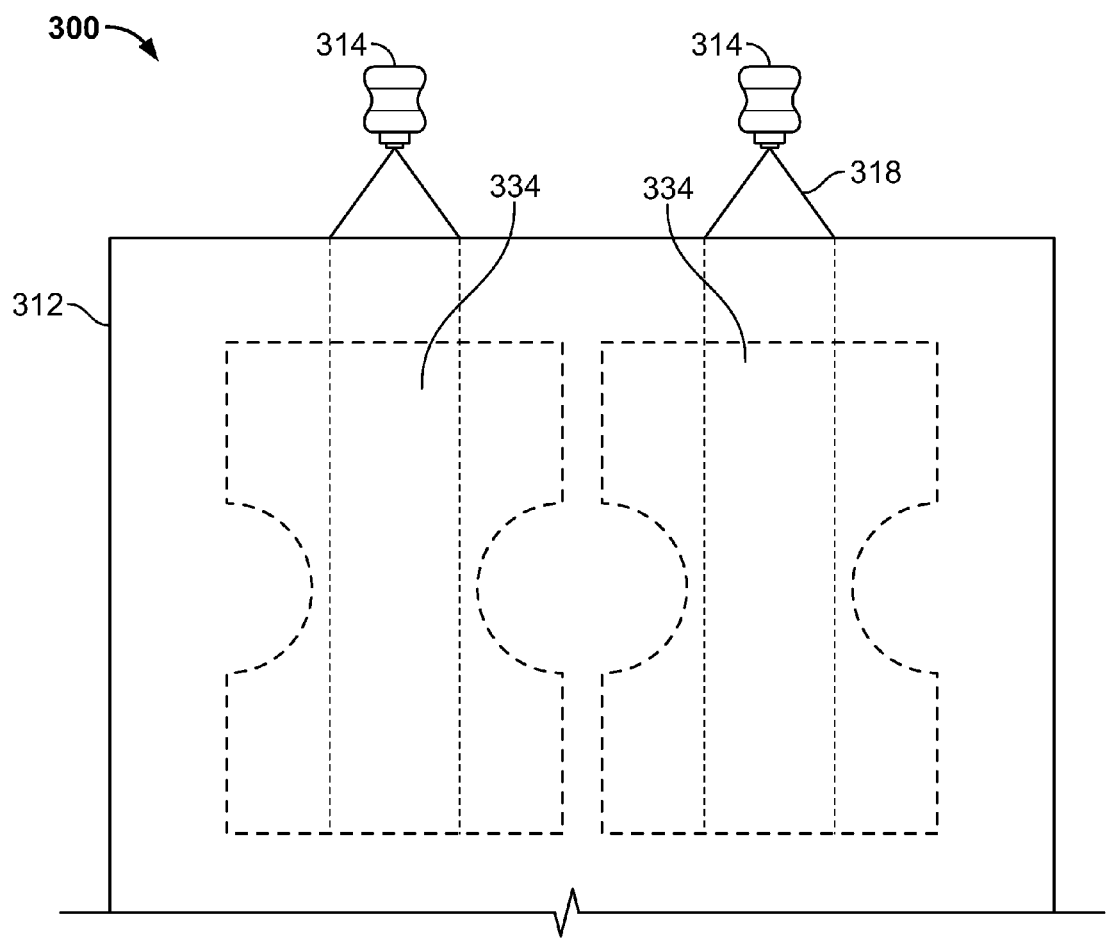
FIG. 6 illustrates a top view of a spraying process according to one embodiment.

According to an alternative embodiment, the chemical coating 318 can be deposited on the appropriate portion(s) of the outer web 312 by a spraying process 300 as shown in FIG. 6. In the illustrated embodiment, two outer layers will be produced across the width of the outer web 312; however, it is contemplated that any number of outer layers can be produced across a width of the outer web 312 depending upon the size of the diaper 10 and the width of the outer web 312. Each of the outer layers will have a corresponding central portion 334. Two spray nozzles 314 are coupled to a reservoir (not shown) containing the chemical coating 318. As the outer web 312 passes beneath the spray nozzles 314, the chemical coating 318 is sprayed onto the outer web 312. The two spray nozzles 314 are disposed above the outer web 312 so that the chemical coating 318 is only sprayed onto the portions of the outer web 312 that correspond to a central portion 334 of the outer layers that will be produced from the outer web 312. It is contemplated that according to some embodiments the chemical coating 318 can be sprayed from the sprayers 314 in foam form. Specifically, chemical coating 318 can be printed (i.e., sprayed through small spray nozzles in close proximity to a target surface) onto the outer web 312 to precisely apply the chemical coating 318 to the outer web 312. Optionally, the outer web can be placed in an oven to dry the chemical coating applied by the kiss roll process, the spraying process, or any other suitable application process.

At this point in the manufacturing process, an inner web, an absorbent pad, and an outer web have been formed. At block 110, the absorbent pad is interposed between the inner web and the outer web by, for example, feeding the absorbent pad onto a conveyor with the outer web and then feeding the inner web into place above the absorbent pad. At block 112, the interposed layers are joined by a suitable means such as, for example, gluing, heating, calendaring, ultrasonic welding or the like. If not integrally formed, at block 114, the fixed ends of the fastening components are secured to the inner layer 20, the outer layer 12 or both by, for example, gluing, heating, calendaring, ultrasonic welding or the like. Optionally, elastic bands may be added as well to facilitate a snug fit and prevent leakage. The assembled layers are then cut into individual diapers. The diapers are cut to a shape and size desired for the anticipated end users (e.g., infants, children, and/or adults).

It will be appreciated by those skilled in the art that many of the steps for manufacturing the diaper or other absorbent article can be performed in a different order than that described above. For example, the absorbent layer 22, the inner layer 20, and the outer layer 12 can be formed in any order. Additionally, it is contemplated that the outer layer 12 can be chemically treated after interposing the absorbent layer 22 between the inner layer 20 and the outer layer 12 or after joining the inner layer 20, the absorbent layer 22, and the outer layer 12.

While the present invention has been described with reference to one or more particular embodiments, those skilled in the art will recognize that many changes may be made thereto without departing from the spirit and scope of the present invention. Each of these embodiments and obvious variations thereof is contemplated as falling within the spirit and scope of the claimed invention, which is set forth in the following claims.

What is claimed is:

1. A method of determining whether an absorbent article is too large for a wearer comprising:

positioning the article on the wearer, the article comprising a back portion and a front portion, an outer layer having a central portion between two side portions, an inner layer, an absorbent layer interposed between the outer layer and the inner layer, and one or more fasteners located on the back portion of the article, the one or more fasteners securing the back portion of the article to the front portion of the article, the central portion of the outer layer being treated with a chemical that substantially inhibits attachment of the one or more fasteners to the central portion of the outer layer;

pressing the one or more fasteners to the outer layer of the front portion such that the back portion is stretched to form a snug fit around the wearer; and determining whether the article should be downsized based on whether the one or more fastener components remain attached to the outer layer of the front portion.

2. The absorbent article of claim 1, wherein the chemical comprises one or a combination of an acrylics, vinyls, urethanes, epoxies, fluorocarbon polymers, and silicone binders.

3. The absorbent article of claim 1, wherein each of the one or more fasteners comprises a plurality of hooks, the plurality of hooks being attachable to fibers of the outer layer that are not chemically treated.

4. The absorbent article of claim 1, wherein the outer layer is a non-woven fabric.

5. The absorbent article of claim 1, wherein the chemical includes a colorant.

6. The absorbent article of claim 1, wherein the one or more fasteners are integrally formed with the back portion.

7. The absorbent article of claim 1, wherein the one or more fasteners are attached to and extend from the back portion.

8. The absorbent article of claim 1, wherein the outer layer comprises polyethylene.

* * * * *